United States Patent [19]

Connolly

[11] Patent Number: 4,933,278
[45] Date of Patent: Jun. 12, 1990

[54] METHOD OF DETERMINING THE NUMBER OF CELLS IN CELL CULTURE

[75] Inventor: Daniel T. Connolly, Manchester, Mo.

[73] Assignee: Monsanto Company, St. Louis, Mo.

[21] Appl. No.: 7,320

[22] Filed: Jan. 28, 1987

Related U.S. Application Data

[63] Continuation-in-part of Ser. No. 736,996, May 22, 1985, abandoned.

[51] Int. Cl.$^5$ .................. C12Q 1/02; C12Q 1/42
[52] U.S. Cl. ......................... 435/29; 435/21
[58] Field of Search ........... 435/21, 29; 436/63, 436/174, 177, 178

[56] References Cited

U.S. PATENT DOCUMENTS 3,002,893 10/1961 Babson .................. 195/103.5

OTHER PUBLICATIONS

Guilbault, Enzymatic Methods of Analysis, Pergamon Press, 1970, p. 71.
Jauregui et al., In Vitro, 17(12), 1100–1110 (1981).
Duncan et al., Clin. Chem. 28(4), 749–55 (1982).
Connolly et al., Anal. Biochem. 152, 136–140 (1986).
Kaighn, Natl. Cancer Inst. Monogr., 49 (Workshop Genitourin. Cancer Immunol. 1976), 59–60.
Laughton, Anal. Biochem. 140, 417–423 (1984).
Barman, Enzyme Handbk., vol. II, Springer-Verlog, N.Y., 1969, 523–4.
A. V. Roy et al., Clinical Chemistry 17(11): 1093–1102 (1971).
Bergmeyer, "Enzymes 2: Esterases, Glicosidases, Lyases, Ligases", in Methods of Enzymatic Analysis, vol. IV, 3rd Edition (Verlag Chemie, Weinheim), pp. 92–101, Mar. 1984.

Primary Examiner—Esther M. Kepplinger
Attorney, Agent, or Firm—Scott J. Meyer; James W. Williams, Jr.

[57] ABSTRACT

A method is disclosed for determining the number of cells in cell culture which comprises lysing the cells and incubating the cell lysate with p-nitrophenyl phosphate for a predetermined period of time at acid pH and at 35°–38° C., and then measuring the color development at 400 to 420 nanometers and comparing with a control. The method is accurate, sensitive, and well-suited for automation, and thereby provides for the rapid sampling of large numbers of cell culture where the cells are grown under very sparse conditions.

7 Claims, 1 Drawing Sheet

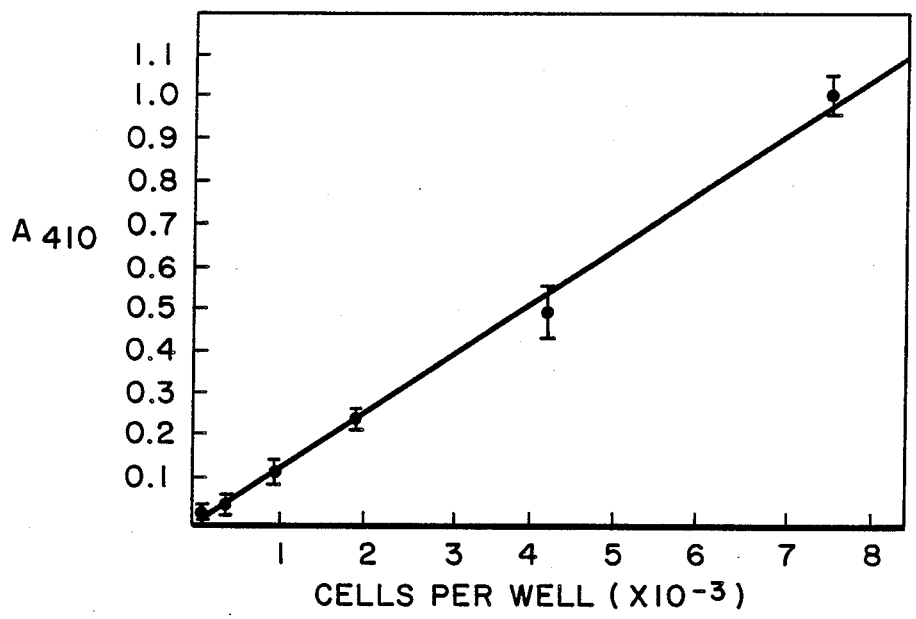

METHOD OF DETERMINING THE NUMBER OF CELLS IN CELL CULTURE

CROSS-REFERENCE TO RELATED APPLICATION

This is a continuation-in-part of copending application Ser. No. 736,996, filed May 22, 1985, now abandoned.

BACKGROUND OF THE INVENTION

This invention relates to a sensitive method of determining the number of cells in cell culture, that is, a method which is adaptable to determining cell counts in levels as low as about 100 to about 1000 cells.

Various process parameters are of substantial importance in cell and tissue culture. One of these parameters is the determination of the number of cells or cell count. This is an important quantitative criterion for estimating the amount of growth or survival in a cell population during culture or maintenance of the cells.

Cells can be determined directly by enumeration of the cell number by means of a haemocytometer, a microscope or an electronic particle counter such as, for example, a Coulter ® electronic cell counter.

One method of estimating viable cells is to determine the proportion of individual cells which can give rise to cell colonies, that is, by determining the plating efficiency. However, this generally is a slow and cumbersome process.

Indirect determination of cells can be made by measurement of packed cell volume, by chemical determination of a cellular component, for example, protein or deoxyribonucleic acid, or by uptake of a chromogenic dye such as neutral red. Another method of determination involves measurement of cellular lactate dehydrogenase activity by reaction with the coenzyme AND, which can be followed spectrophotometrically, as described, for example, by Jauregui et al., *In Vitro* 17(12), 1100–1110 (1981).

Although the foregoing methods are useful in many cases, they have been found inconvenient or unsuitable in certain instances either because they are time consuming, cumbersome or not adaptable to the determination of large numbers of samples, especially where the cells are grown under very sparse conditions and where sensitivity is an important consideration. That is, conventional methods are not generally adaptable to determining the number of cells in cell culture at sensitivity as low as about 100 to about 1000 cells, but, instead, are usually adaptable only to higher cell counts.

BRIEF DESCRIPTION OF THE INVENTION

In accordance with the present invention a novel and sensitive method has been developed for determining the number of cells in cell culture. The method comprises lysing the cells and incubating the cell lysate with p-nitrophenyl phosphate for a predetermined period of time at pH less than about 7 at about 35° to 38°C., and then measuring the color development at 400 to 420 nanometers and comparing with a control. This method provides sensitivity as low as about 100 to about 1000 cells.

The method of the invention is based on the presence of acid phosphatase in the cells. The p-nitrophenyl phosphate is a substrate for the acid phosphatase which provides for an enzymatic hydrolysis that can be measured colorimetrically. The number of cells has been found to be substantially directly proportional to the amount of acid phosphatase thus measured. The method of the invention thus is applicable to cells that contain acid phosphatase.

Use of p-nitrophenyl phosphate as a substrate for the colorimetric assay of acid phosphatase is known. The cleaved product, p-nitrophenol, is yellow in alkaline solution and its color intensity measured at 400 to 420 nanometers is proportional to phosphatase activity. See for example, Guilbault, *Enzymatic Methods of Analysis*, Pergamon Press, 1970, p. 71 and references cited therein. However, it is not believed that this substrate has been used heretofore in a method of counting cells as defined herein. Its prior use has been in the diagnostic assay of acid and alkaline phosphatase levels in blood serum and the like diagnostic procedures. However, in diagnostic procedures, the desired goal is measurement of enzyme level, not cell number as desired herein. See, for example, Kaighn, *Natl. Cancer Inst. Monogr.* 49 (*Workshop Genitourin. Cancer Immunol.*, 1976), 59–60, which discloses assay for the acid phosphatase enzyme level in cells as an adjunct to cancer diagnosis. Kaighn uses thymolphthalein monophosphate as the enzyme substrate and measures at 590 nanometers, which is said to be more specific than p-nitrophenyl phosphate, but requires from $10^6$ to $10^7$ cells for the diagnostic procedure.

DETAILED DESCRIPTION OF THE INVENTION

While the specification concludes with claims particularly pointing out and distinctly claiming the subject matter regarded as forming the invention, it is believed that the invention will be better understood from the following detailed description of preferred embodiments of the invention taken in connection with the accompanying drawing in which:

FIG. 1 is a graphical representation showing linear proportionality between number of cells per well and colorimetric absorption at 410 nanometers ($A_{410}$) in one embodiment of the invention.

The determination of the number of cells in accordance with the present invention can be made at any convenient time during the cell culture period in which it is desired to follow the growth or survival of the cells. These cells can be growing in conventional tissue culture flasks such as, for example, T-flasks, roller bottles, flat bed chambers, hollow fiber reactors, agitated suspension culture vessels and the like cell culture devices under various suspension or anchorage-dependent cell culture conditions. The time and frequency of the cell counts will depend upon the nature of the specific cells being cultured, their normal growth period, the cell products sought after and other such factors. By following the cell count in accordance with the invention one can readily determine the growth phase or stage in which the cells exist at any given time. This is an important determination for maintaining product uniformity and maximum economic production.

Examples of cells which are known to have an acid phosphatase content and, therefore, are readily adaptable to the method of the present invention are mammalian cells such as liver, spleen, prostate gland and endothelial cells. Other cells such as fibroblasts and hybridoma cells also can be estimated in accordance with the invention.

When the cells are grown in suspension culture, the counting efficiency will be increased by thorough mixing and rapid sampling since cells in suspension tend to settle out very rapidly. Multiple counts are preferable insofar as they will help to establish increased confidence in the count and will provide greater statistical accuracy and reliability.

The method of the invention is particularly adaptable to determination of cells in small numbers such as in microwell tissue culture plates. These plates generally contain from 6 to 96 wells per plate and can accomodate as little as a fraction of a milliliter of cells or cell lysate per well, for example, 0.2 ml. Use of such plates are advantageously adaptable to automation and, thus, the method of the invention likewise is adaptable to automation. Such plates have been typically used heretofore in immunoassays such as the enzyme linked immunosorbent assay (ELISA). As adapted for use in the present invention, the microwell tissue culture plates containing the lysed cells incubated with p-nitrophenyl phospate can be placed in commercially available instruments for measuring absorbance through the plate. Such instruments project a vertical beam of light at an appropriate wavelength through the transparent plate to a detector. An example of such an instrument is the Microplate Reader, Dynatech ® model MR600, available from Dynatech Laboratories, Inc., Alexandria, VA. This instrument counts 96 wells of cells in approximately one minute, and can be interfaced with a computer for data analysis.

Lysing of the cells to form a lysate for incubation with the p-nitrophenyl phosphate can be by mechanical disruption bu preferably by chemical action such as by treatment with saline, phosphate buffered saline (PBS) or lactated Ringer's solution in the presence of detergents, for example, Triton ®X-100 which is a commercially available nonionic octylphenoxy polyoxyethanol.

Incubation is preferably carried out at pH and temperature conditions of maximum enzyme activity. The acid phosphatases have optimal activity at acid pH and the preferred range used herein is from about 4.5 to about 5.5. The preferred temperature range is from about 35°C. to about 38°C. and most preferably at about 37°C.

Only a small amount of the p-nitrophenyl phosphate need be used in the incubation reaction. From about one to about 20 millimolar p-nitrophenyl phosphate is preferred.

Following incubation for a predetermined period of time the enzymatic reaction is stopped and the absorbance at 400 to 420 nanometers is determined. Incubation for about ten to about 180 minutes is particularly suitable but about two hours is generally preferred. Cessation of the hydrolytic reaction can be achieved by addition of enzymatic inhibitors or by adjusting to a pH level at which the enzyme is inactive. Adjusting to alkaline pH by addition of alkali such as NaOH is convenient for this purpose.

A control chart can be developed as in FIG. 1 by determining the number of cells per well or other unit of cells in at least three different levels and plotting against absorbance to form a straight line relationship. The number of cells for any cell culture of the given cells can then be estimated by carrying out the method of the invention and comparing against the control chart.

The following examples will further illustrate the invention although it will be understood that the invention is not limited to these specific examples.

EXAMPLE 1

Cell Culture. Fetal bovine aortic endothelial cells were obtained as described by Olander et al, *In Vitro* 18, 99–107 (1982); Feder et al, *J. Cell Physiol.* 116, 1–6 (1983). The cells were maintained in 75 $cm^2$ flasks (Falcon) with Dulbecco's modified Eagle medium (DMEM) supplemented with 10% (v/v) calf serum(-Gibco). Stock cultures were split 1:3 weekly, with medium changes twice weekly. Cells were used between passages 10 and 18. For growth assays, cells were plated onto 0.32 $cm^2$ flat bottom 96-well plate (Costar) in 0.2 ml DMEM plus 10% (v/v) calf serum.

Acid Phosphatase Assay. Cells were grown in 96-well plates at densities between 100 and 10,000 cells per well for acid phosphatase assay. The medium was removed by vacuum aspiration, and each well washed once with 200 microliters of PBS using a multichannel pipettor (Flow Laboratories). Then, to each well, 100 microliters of buffer were added containing 0.1M sodium acetate, pH 5.5, 0.1% Triton X-100, and 10mM p-nitrophenyl phosphate (Sigma 104 Phosphatase Substrate). A repeating pipet (Eppendorf Brinkman model 226-006 was usually used for this addition. The plates were placed in a 37°C. incubator for two hours. The reaction was stopped with the addition of 10 microliters 1N sodium hydroxide, and color development determined at 410 nM using a rapid Microplate Reader (Dynatech model MR600 . The first well of each plate contained only buffer and was used as a blank. The amount of non-enzymatic hydrolysis of substrate was determined for each assay by including wells that did not contain cells. This background value was usually about 0.065±0.005 absorbance units. The background value was subtracted from all experimental values.

Cell Number. For control and comparative purposes, cell number was determined following trypsinization (0.05% wt/vol; Worthington Diagnostic Systems, Inc.) either by using a haemocytometer, or by electronic particle counting using an Elzone XY counter (Particle Data, Inc.). The two methods agreed to within 10%. In order to determine the low numbers of cells seeded in the 0.32 $cm^2$ wells, it was necessary to pool cells from replicate cultures before particle counting. This was accomplished by adding 0.1 ml of trypsin solution to each well to detach the cells, adding the contents of each well to the next subsequent well until the cells from eight wells had been pooled, and then washing each well, again sequentially, with PBS. The actual cell number was determined after substraction of the number of particles detected in wells that had been treated in the same way, including incubation with medium, but containing no cells. By this method, it was possible to reliably detect about 100 cells per well.

The bovine aortic endothelial cells were found to contain an active acid phosphatase. Cells were plated onto the 96-well culture plates at two different concentrations, then after one day, the cellular acid phosphatase was measured in each well. Although the reaction appeared to be biphasic, the activity was dependent upon cell number. The optimum pH for the reaction was determined to be pH 5.5 and an apparent Km for p-nitrophenyl phosphate estimated to be about 1 mM.

In order to determine if acid phosphatase activity could be used to quantitate the number of endothelial cells in culture, cells were seeded at different densities onto 96-well plates. The next day, replicate cultures were used for either cell number determination by electronic particle counting, or for acid phosphatase assay (FIG. 1). A linear relationship was obtained between cell number and enzyme activity. The bars over and under the determined points on the curve in FIG. 1 show the standard deviations from the points. The sensitivity of the assay was excellent, with as few as 100 cells per well detectable using a two hour assay. Fewer cells can be detected by extending the reaction time. Since the assay was linear to about 10,000 cells per well, this method provides a wide range for cell number determination and thus is applicable for many different cells and cell culture conditions.

Estimation of the number of fetal bovine endothelial cells as in the foregoing Example 1 is particularly useful in conjunction with measuring the stimulation of cellular growth factors derived from cultured human tumor cells or other sources. See Olander et al., *In Vitro* 18(2), 99–107 (1982).

EXAMPLE 2

Substantially similar results as in Example 1 were obtained by using human foreskin fibroblast cells in the method of said example instead of fetal bovine aortic endothelial cells. A lower limit of about 500 cells per well were detected by this assay. Although the assay for the fibroblast cells in this example was slightly less sensitive than in the case of the endothelial cells of Example 1, it was substantially better than the lower limit of sensitivity of about 2000–5000 cells per well in conventional methods.

EXAMPLE 3

In order to demonstrate the advantageous sensitivity obtained by the method of the present invention for cell counting over the prior art procedure for diagnostic measurement of enzyme level, the method of the present invention was compared to the procedure of Kaighn, *Nat'l. Cancer Inst. Monoqr.* 49 (*Workshop Genitourin. Cancer Immunol.*, 1976), 59–60. For use in this comparison, human foreskin fibroblasts (AG 1523, Institute for Medical Research, Camden, N.J.) were selected as representative of the type of cells used by Kaighn. These cells were initially cultured in DMEM with 10% fetal calf serum and grown in T-flasks as in Example 1.

One portion of the cultured cells (sample A) was then used in the acid phosphatase assay and cell number determination as in Example 1.

Another portion of the cultured cells (sample B) was treated in the manner described by Kaighn in which the cells were buffered to pH 7(Tris, 0.01 M; NaCl, 0.1 M; Tergetol ® NP-40 nonylphenol ethoxylate surfactant 1%) and suspended by Vortex at 10 seconds/minute for 25 minutes, and then citrate buffer (0.01 M, pH 6) was added to a final volume of about 0.5–1 ml. The supernatant was assayed for acid phosphatase enzyme using 2.2 mM thymolphthalein monophosphate in 0.1 M citrate buffer with 5g Brij ®-35 per liter, pH 6.0), incubating at 37°C. and measuring absorbance at 590 nanometers.

In sample A using the method of the present invention, a level of 1000 cells was readily determined by the absorbance reading of 0.01. By way of comparison, in sample B using the method of Kaighn, a level of at least about $2-3 \times 10^5$ cells was required to produce a comparable absorbance reading of 0.01. Reduction of the number of cells to a level of about $4 \times 10^4$ cells in the Kaighn method produced an absorbance reading essentially identical to the background or control level of no cells. These results thus confirm that the method of cell counting according to the present invention is about 200 to 300 times as sensitive as the method described by Kaighn for diagnostic measurement of enzyme level.

Various other examples will be apparent to the person skilled in the art after reading the disclosure herein without departing from the spirit and scope of the invention and it is intended that all such other examples be included within the scope of the appended claims.

What is claimed is:

1. A color-sensitivity method for determining the number of cells in in vitro cell culture at a sensitivity as low as about 100 or about 500 cells which comprises lysing the cells and incubating the lysate with p-nitrophenyl phosphate at acid pH for a predetermined period of time at a temperature of from about 35° to about 38°C. and then measuring the color development at 400 to 420 nanometers and correlating said color development with cell number by comparing with a control standard of known cell number.

2. The method of claim 1 in which the incubation pH is from about 4.5 to about 5.5.

3. The method of claim 1 in which the incubation temperature is about 37°C.

4. The method of claim 1 in which the incubation is carried out for about ten to about 180 minutes.

5. The method of claim 1 in which from about one to about 20 millimolar p-nitrophenyl phosphate is used in the incubation.

6. The method of claim 1 in which the cells are cultured endothelial cells and the sensitivity is as low as about 100 cells.

7. The method of claim 1 in which the cells are cultured fibroblast cells and the sensitivity is as low as about 500 cells.

* * * * *

UNITED STATES PATENT AND TRADEMARK OFFICE
CERTIFICATE OF CORRECTION

PATENT NO. : 4,933,278

DATED : June 12, 1990

INVENTOR(S) : Daniel T. Connolly

It is certified that error appears in the above-identified patent and that said Letters Patent is hereby corrected as shown below:

In col. 1, line 37, "AND" should read --NAD--.

Signed and Sealed this

Twenty-second Day of October, 1991

Attest:

HARRY F. MANBECK, JR.

*Attesting Officer*  *Commissioner of Patents and Trademarks*